Figures 3, 4:
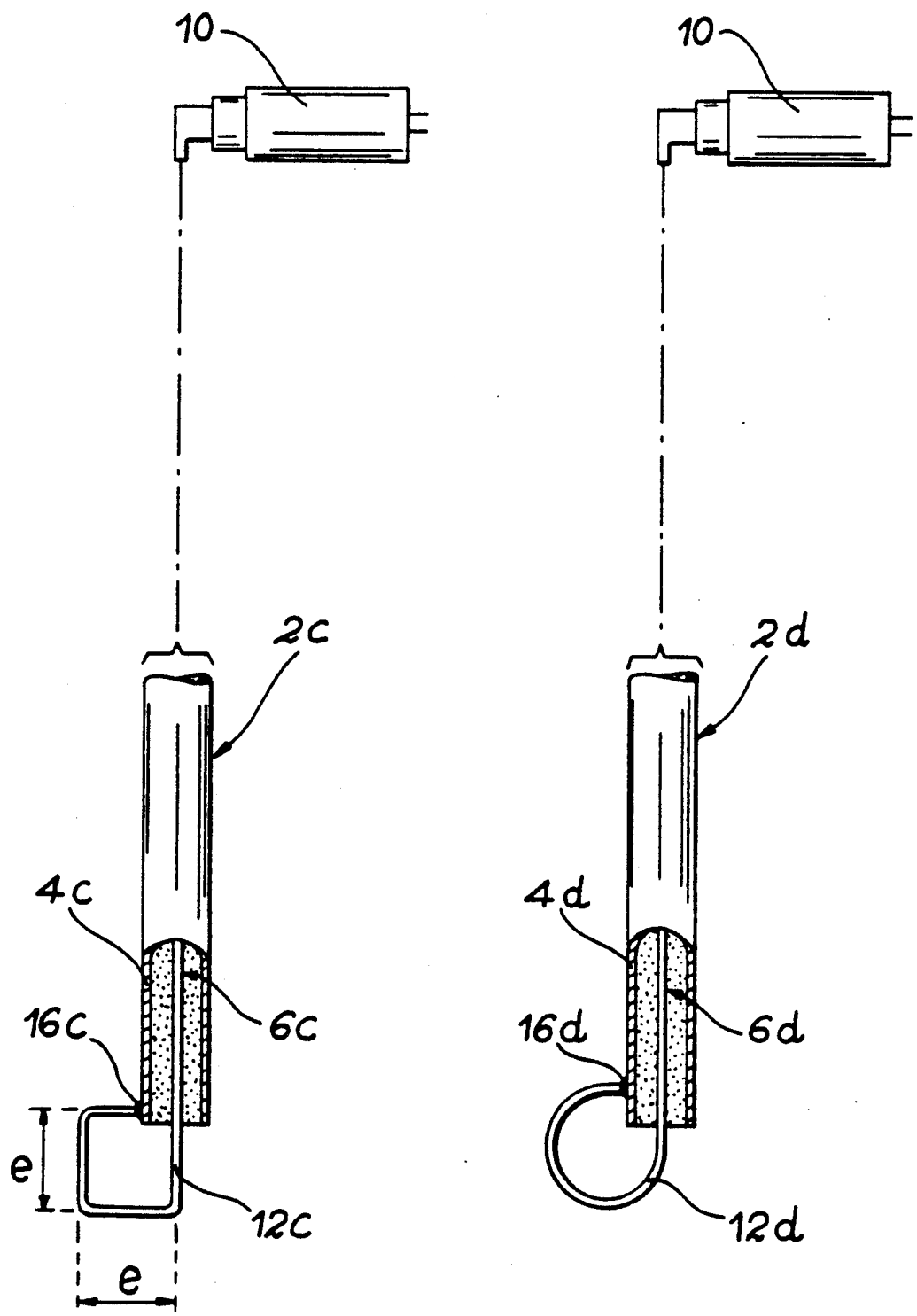

United States Patent [19]

Lacombe et al.

[11] Patent Number: 5,059,914

[45] Date of Patent: Oct. 22, 1991

[54] MICROWAVE DEVICE FOR THE CONTINUOUS MEASUREMENT OF THE VISCOSITY OF A VISCOUS MEDIUM

[75] Inventors: Jean-Francis Lacombe, St Medard en Jalles; Jean-Louis Miane, Pessac, both of France

[73] Assignee: Aerospatiale Societe Nationale Industrielle, Paris, France

[21] Appl. No.: 551,181

[22] Filed: Jul. 11, 1990

[30] Foreign Application Priority Data

Jul. 11, 1989 [FR] France .................................. 89 09307

[51] Int. Cl.$^5$ ...................... G01R 27/04; G01N 22/00
[52] U.S. Cl. .................................... 324/642; 324/632; 324/637
[58] Field of Search ............... 324/632, 637, 639, 640, 324/642, 643, 645, 646, 629; 73/61.1 R, 61 R

[56] References Cited

U.S. PATENT DOCUMENTS

| | | | |
|---|---|---|---|
| 3,701,943 | 10/1972 | Kaiser | 324/585 R |
| 3,851,244 | 11/1974 | Mounce | 324/640 |
| 4,544,880 | 10/1985 | Nagy et al. | 324/642 |
| 4,786,857 | 11/1988 | Mohr et al. | 324/643 X |
| 4,912,971 | 4/1990 | Jeambey | 324/639 X |

OTHER PUBLICATIONS

IEE Transactions on Instrumentation and Measurement, vol. IM-34, No. 3, Sep. 1985, pp. 417–421, New York, U.S.A.; M. Martinelli et al.: "A Method for Dynamic Dielectric Measurements at Microwave Frequencies: Applications to Polymerization Process Studies", *pp. 417–419; FIG. 1, 3*.
Physics in Medicine & Biology, vol. 31, No. 9, Sep. 1986, pp. 1031–1040, London, GB; S. Ray et al.: "Microwave Absorption in Lossy Liquids", *pp. 1034, 1035; FIG. 1*.
Journal of Physics E/Scientific Instruments, vol. 20, No. 7, Jul. 1987, pp. 872–877, Bristol, GB; M. C. Steel et al.: "Precision Waveguide Cells for the Measurement of Complex Permittivity of Lossy Liquids and Biological Tissue at 35 GHz", *pp. 873, 874; FIG. 1, 2*.
Review of Scientific Instruments, vol. 52, May 1981, pp. 767–769, New York, U.S.A.; K. K. S. Jamwal et al.: "Simple and Fast Technique for Measuring Dielectric Constant of Polymers at Microwave Frequencies", *FIG. 2*.

Primary Examiner—Jack B. Harvey
Attorney, Agent, or Firm—Hayes, Soloway, Hennessey & Hage

[57] ABSTRACT

Microwave device for the continuous measurement of the viscosity of a viscous medium. The device includes a microwave source connected via a microwave guide to a sensor essentially incorporating at least one semi-rigid, coaxial microwave guide (2) for immersion in the medium. The cable has an outer sheath (4) and a core (6), which conduct electricity and are arranged coaxially. The space defined between the outer sheath and the core is filled by a dielectric (8). The core has a bare end (12) for placing in contact with the viscous medium. The sensor is intended to produce in the medium incident microwaves of a given power level, and to detect the power of the microwaves reflected by the medium. A second microwave guide (10) is provided for coupling the detector to the sensor.

14 Claims, 4 Drawing Sheets

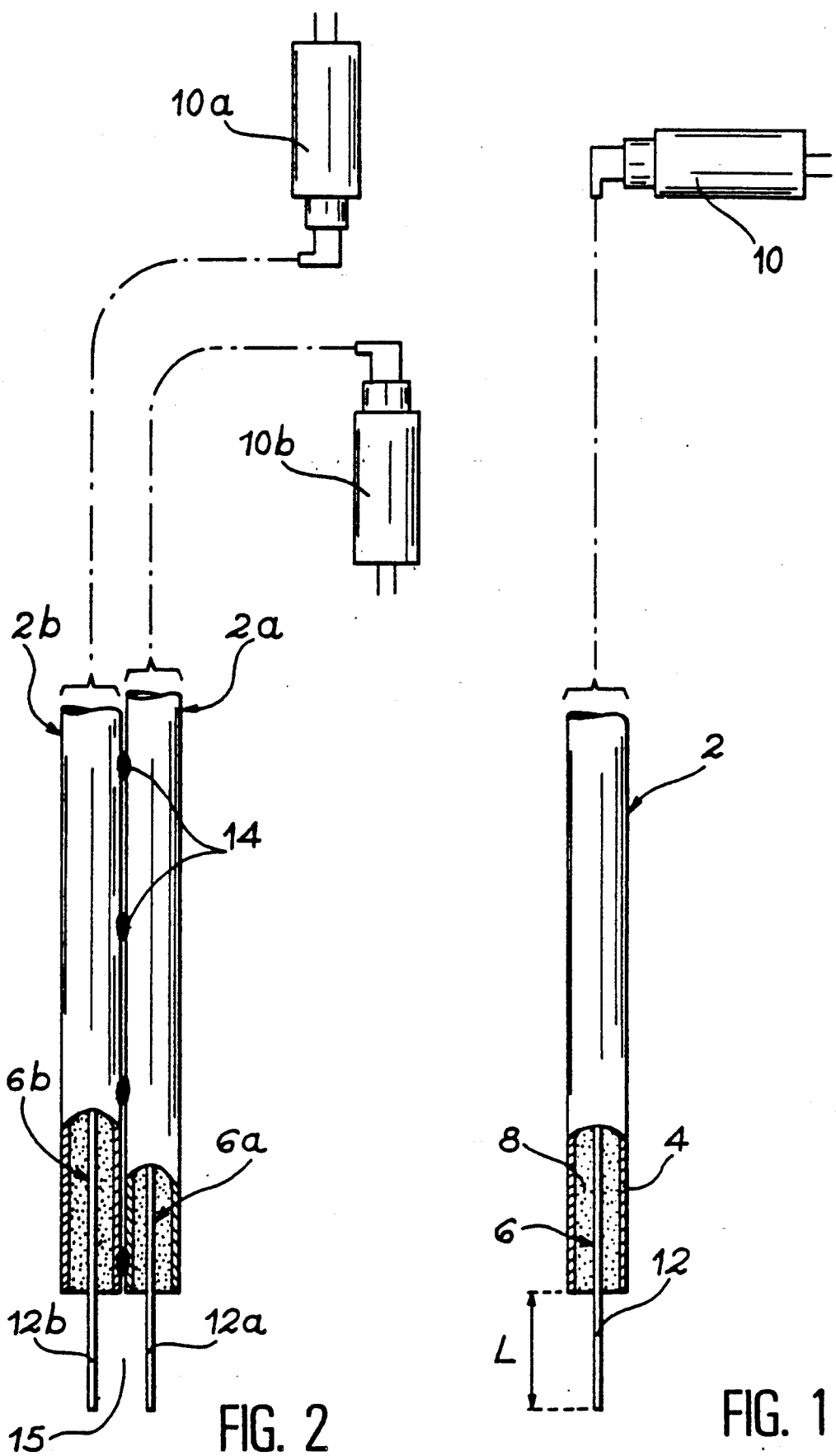

MICROWAVE DEVICE FOR THE CONTINUOUS MEASUREMENT OF THE VISCOSITY OF A VISCOUS MEDIUM

DESCRIPTION

The present invention relates to an industrial microwave device for the continuous, real time measurement of the viscosity of a viscous medium.

The invention can be used for measuring the viscosity of all polar liquid media and in particular all polymers containing dipolar elements. More specifically, the invention makes it possible to continuously check the evolution of the viscosity of the resins used for the production of high performance composite materials during the polymerization and/or crosslinking thereof. These composite materials are used for producing parts in the automobile, aeronautical and space fields. In particular, the invention applies to phenolic, polyurethane, polyester and epoxy resins, as well as to polymers containing dipolar elements, e.g. $>C=O$,

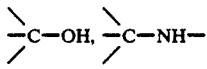

groups.

In the field of composite materials, it is very frequent practice to use substrates (made from Kevlar, glass, aramide or carbon fibres), which can be impregnated with a resin in an impregnation chain calibrating the resin percentage. In order to control the quality of the product, the said substrate is impregnated with a constant viscosity resin. As the viscosity of the resin is linked with its temperature, it is desirable to control the resin temperature during said impregnation stage as a function of its viscosity.

The invention relates to a microwave device having a sensor, which can be immersed in the viscous medium to be measured associated with electronics for processing the signal produced by the sensor in order to follow the evolution in real time of the viscosity of the resin. Such a system can be easily integrated into an installation and makes it possible to automate the production process of composite materials by making the temperature dependent on the resin viscosity. The installation of the sensor in the viscous medium to be checked ensures that the viscosity is checked in situ and in real time.

Although the measuring device is completely suitable for checking the viscosity of a resin used for the production of composite materials, the invention can also be used in all fields requiring a continuous checking of a polar viscous medium.

Conventionally the viscosity of oils or any other viscous liquid is measured with the aid of glass capillary tubes or with the aid of a system of funnels having a certain constant or coefficient corresponding to their calibration. The principle is based on the time taken by a certain liquid quantity to flow freely between two reference marks. This method is more particularly described in FR-A-2 604 271.

The viscosity of a viscous liquid can also be measured with the aid of a rotary viscosimeter of the type described in FR-A-2 587 115, which requires the sampling of the liquid to be studied in a container in which rotates a blade or a cylinder. The measurement principle is based on the determination of the torque linked with the shear force of the viscous product between the blade or rotary cylinder and the container wall.

However, these devices do not permit a continuous, real time checking of a viscous product, in view of the fact that the measurement of the viscosity takes place by sampling. Within the framework of the production of composite materials, said sampling necessarily leads to the stoppage of production and to the intervention of an operator.

In addition, IEEE Transactions on Instrumentation and Measurement IM-34 (1985), September, No. 3 by M. Martinelli et al, pp 417–421 discloses a microwave device for analyzing the polymerization state of a resin, which also involves sampling and which therefore does not permit an in situ, continuous analysis. This device has a resonant cavity able to contain a sample and a microwave source which is dependent on the resonant frequency of the cavity.

The invention relates to an industrial microwave device for the continuous, real time measurement of the viscosity of a viscous medium making it possible to obviate the aforementioned disadvantages. In particular, the device according to the invention has a sensor which can be immersed in the viscous medium, whose viscosity is to be measured and to give a real time measurement without carrying out sampling, which gives a good adaptation to an industrial application, whilst still giving the precise and reproducible results in the same way as the prior art viscosimeters. Furthermore, the device according to the invention is easy to manufacture and easy to operate. Finally, the sensor constituting the same has small overall dimensions.

More specifically, the invention relates to a device for the continuous measurement of the viscosity of a polar viscous medium having a microwave source, a sensor essentially having at least one semi-rigid, coaxial microwave cable for immersion in the medium and connecting means, said cable being constituted by an outer sheath and a core which conduct electricity and which are arranged coaxially, the space defined between the sheath and the core being filled with a dielectric, the core having a bare end which is placed in contact with the viscous medium, said sensor being intended to produce in said medium incident microwaves of a given power and to detect the power of the microwaves reflected by the medium, a detector being provided for transforming the power of the reflected microwaves into an electric signal which is a rising function of the viscosity, a first microwave guide is provided for coupling the microwave source to the sensor and a second microwave guide is provided for coupling the detector to the sensor.

The advantage of a dielectric measurement is to have a simple, stationary sensor, which is easy to maintain and which can in particular follow the complete polymerization process, including the crosslinking phase, when the resin is hardened.

Bare end means an end having no dielectric and outer conductor.

The sensor according to the invention has a reduced size and in particular an external diameter below 5 mm operating in a wide frequency range e.g. between 2 and 18 GHz. The frequency used is a function of the viscous medium to be analyzed and in particular its permittivity.

As a result of the baring of the end of the core to be placed in contact with the viscous medium to be checked, it is possible to ensure an ultra-high frequency coupling between the sensor and the medium. The coaxial cable core bare end can be rectilinear or shaped like a magnetic loop closed in short-circuit form with the outer conductive sheath.

Physics in Medicine and Biology, vol. 31, No. 9, September 1986, pp 1031-1040 by S. Ray and J. Behari discloses a rectilinear coaxial sensor for measuring the permittivity of ionic solutions in biology. The method used is a laboratory method, which cannot be transferred to the industrial scale. It makes use of complex impedance measurements on the basis of which the complex permittivity is recalculated on the basis of a network analyzer, the calculations being resolved by means of a microcomputer.

The use of the magnetic loop offers a certain number of advantages. Thus, the size of the magnetic loop permits a better adaptation to a given frequency (i.e. maximum sensitivity at said operating frequency). Moreover, with the loop, the best sensor/medium interaction makes it possible to obtain a more stable response (power reflected as a function of the microwave frequency). Finally, the mechanical behaviour of the sensor with the magnetic loop is less fragile as a result of its better rigidity.

The length of the bare end is a function of the viscous medium to be studied and in particular its permittivity. For example, for a use frequency of 2 to 4 GHz, the bare end length is between 2 and 2.5 cm and it is used for materials having low dielectric permittivities (e.g. close to that of air). For higher dielectric permittivities, such as for epoxy resins generally used in the production of composite materials, the tendency is to use a frequency of 9 to 10 GHz. In this case, the optimum length of the bare end of the coaxial cable core is $10 \pm 2$ mm.

The sensor of the device according to the invention can have two joined coaxial cables, one being used for carrying the incident microwaves and the other for the microwaves transmitted by the medium, whose viscosity is measured. However, it is preferable to use a single coaxial cable in order to improve the microwave coupling between the sensor and the medium whose viscosity is measured.

The materials constituting the sensor according to the invention must be chemically compatible with the medium to be analyzed and must in particular be chemically resistant with respect to said medium. In the case of an epoxy resin or glycerol, it is advantageous to use a sensor having a core and an outer sheath made from copper, optionally protected by silver or chromium plating.

The material constituting the dielectric can be any random dielectric conventionally used in the ultra-high frequency field. However, in order to obtain an impedance of 50 ohms adaptable to most measuring devices using microwaves, use is generally made of polytetrafluoroethylene, generally known under the trade name Teflon.

The principle of measuring the viscosity is based on the power of the microwaves reflected by the viscous medium, said microwave reflection being due to the sudden impedance change caused by the discontinuity between the coaxial structure of the sensor and the medium to be checked. Moreover, the power of the microwaves reflected by the viscous medium is a function of its permittivity, which is dependent on the temperature of the medium. Furthermore, in .the case of a resin, the permittivity is dependent on its polymerization state. At a given temperature, the permittivity of the resin decreases as the resin polymerizes. Thus, at a given temperature, on the basis of the evolution of the reflected microwave signal, it is possible to follow the viscosity state of the resin during its polymerization.

The sensor of the device according to the invention is immersed in the medium whose viscosity is to be measured, so that an interaction volume perfectly defined by the shape of the sensor end is obtained and is always the same.

The sensor of the device according to the invention, which can be easily disassembled and then reassembled, always gives the same signal. The two sensors based on the same model also give the same signal. This means that the sensor according to the invention is reliable over a period of time.

The special nature of the invention is that the measurement of the reflected microwave power leads to a simple, inexpensive measuring device. For example, a phase measurement would require costly laboratory equipment and network analyzers.

The invention applies to viscous, i.e. more or less liquid media (pregelling state prior to polymerization). The crosslinking method is not involved in the measurement, no matter whether it is of an ionic or radical nature. In addition, the attachment method of the molecules and the polar elements thereof is not involved in the polymerization measurement.

Advantageously, said measuring device also comprises an insulator and an attenuator of the microwave power, which are connected between the microwave source and the directional coupler. This permits a standardization of the operating conditions of the devices according to the invention indispensable in industrial use. The measuring device also has a filter for filtering the electric signal supplied by the detector.

The invention is described in greater detail hereinafter relative to non-limitative embodiments and the attached drawings, wherein show:

FIGS. 1 to 4 Different embodiments of the coaxial sensor according to the invention.

Figure 5:
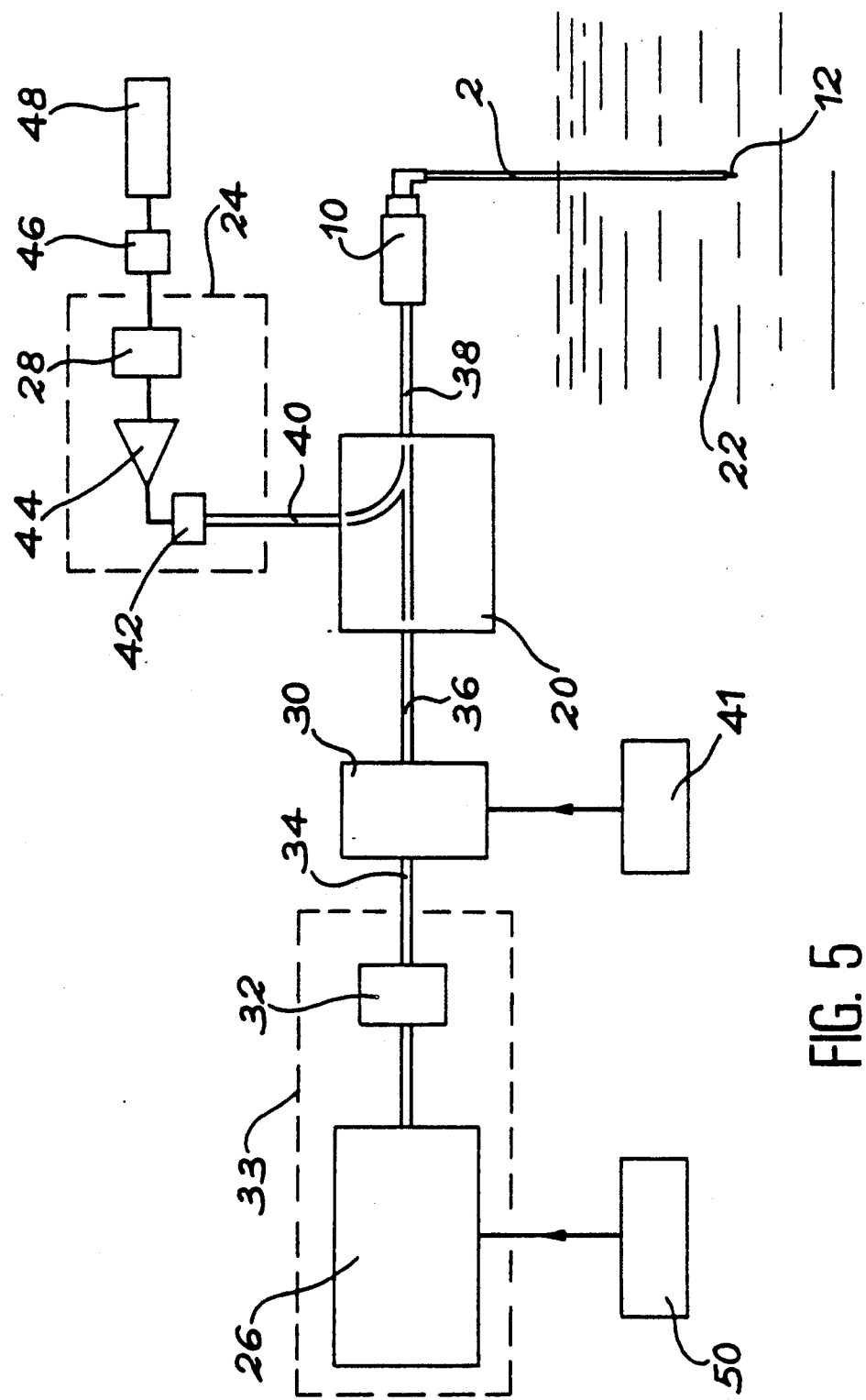

FIG. 5 Diagrammatically a device for the continuous measurement of the viscosity of a polar medium according to the invention.

Figure 6:
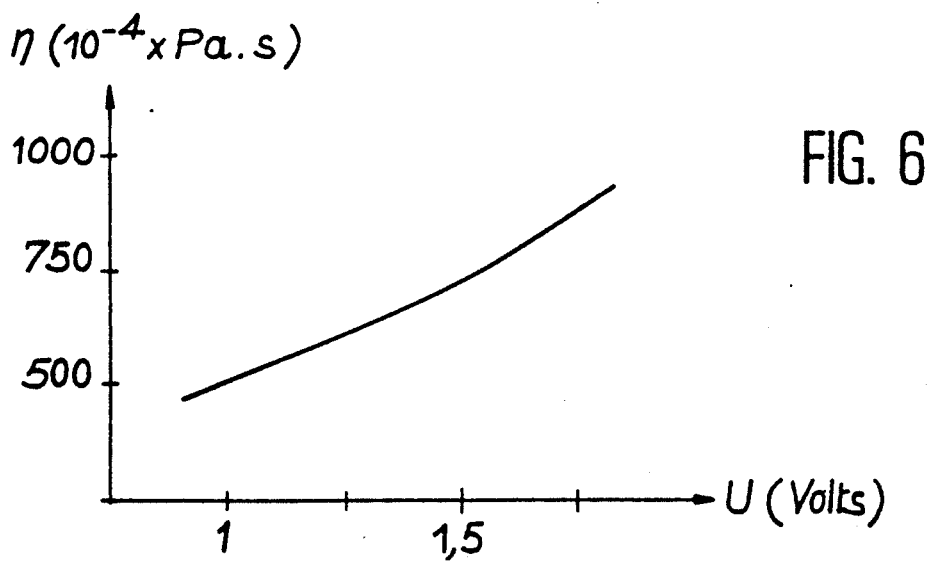

FIG. 6 Variations of the viscosity as a function of the voltage supplied by the detection system of the measuring device according to the invention in the case of glycerol.

Figure 7:
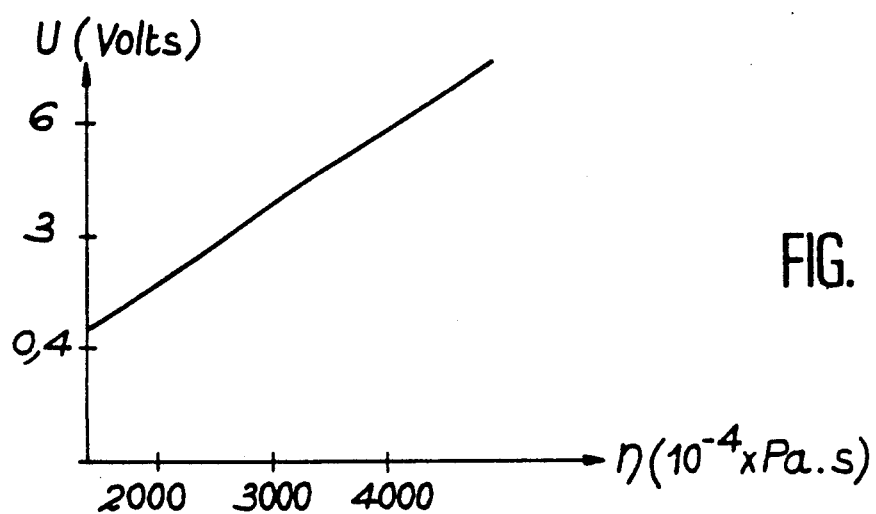
Figure 8:
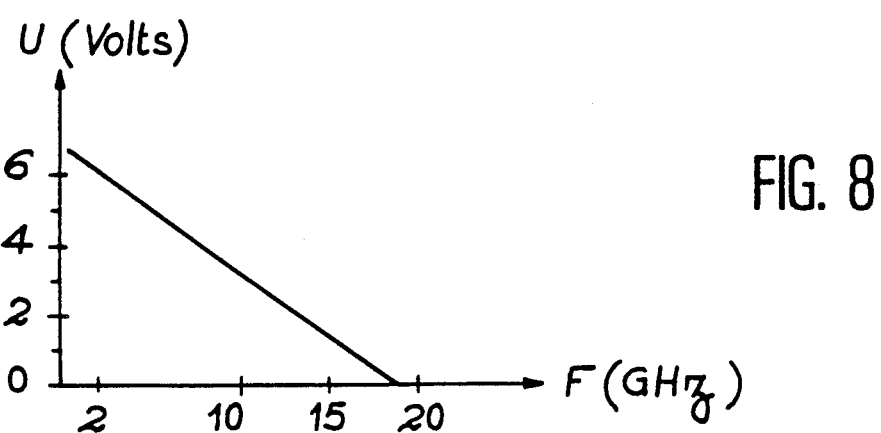

FIGS. 7 and 8 Curves illustrating the sensitivity of the sensor as a function of the microwave frequency during the measurement of the viscosity of an epoxy resin.

Before describing the various embodiments of the sensor according to the invention, the physical principle involved will be defined.

The dielectric properties of liquid media are dependent on the structure of the molecules forming them. Non-polar liquids, such as benzene have a real permittivity independent of the measurement frequency. The medium does not absorb the microwaves and its permittivity is only dependent on the temperature or pressure via the expansion of the medium. However, when the molecules have a permanent dipole moment, the permittivity of the medium is a function of the measurement frequency due to the relaxation phenomena, the movement of the molecular dipoles being impeded by interactions between molecules.

For example, water is such a medium. At low frequencies it has a high permittivity equal to 81 and the dipolar relaxation is in the GHz range with an absorption maximum at about 20 GHz at ambient temperature. This phenomenon is characterized by a relaxation time t and a simple model (DEBYE model) makes it possible to express the permittivity of the medium as a function of this relaxation time, namely $t = K\eta$ in which K is a characteristic constant of the medium.

The mobility of the dipoles is dependent on their environment and any change therein leads to modifications of the relaxation times and the permittivity. Thus, the permittivity of a polar liquid is dependent on its viscosity. Thus, it is possible to replace a viscosity measurement by a permittivity measurement at a frequency in one of the relaxation ranges of the liquid.

Thermosetting resins are more complex media, because the formulations used generally contain several molecule types, namely oligomers of different masses, hardeners and adjuvants. Nevertheless, the molecules constituting the mixture carry dipolar segments which lead to relaxations in high and ultra-high frequencies.

The macroscopic state of a resin can be characterized by its viscosity, which is a function of the temperature and the average weight or mass of the molecules. The viscosity is a consequence of the molecular interactions and therefore a viscosity change is a manifestation of variations in the dipolar movement possibilities and consequently the times of the relations. These different dependencies are expressed by a group of relations between the viscosity, temperature, mean weight, relaxation time and permittivity.

On the basis of these relations, it is possible to express the permittivity of a resin as a function of its viscosity. However, said relation is very complex and the intermediate terms such as the mean weight and the relaxation time are poorly defined and difficult to measure. It is therefore faster to experimentally determine the permittivity/viscosity relation. This must be repeated for each resin or formulation.

The permittivity of a viscous medium is measured in the laboratory by guide or cavity measurements on samples, but these methods are not very suitable for industrial use. Therefore the inventors have developed sensors and devices having a simple construction not making it possible to measure the permittivity, but which give information (reflection coefficient or transmission coefficient) directly linked with the permittivity of the medium and its viscosity.

Various embodiments of the sensor according to the invention are shown in FIGS. 1 to 4.

The sensor shown in FIG. 1 is constituted by a semi-rigid, coaxial microwave cable 2 formed from an electricity conducting, outer sheath 4 and a core 6, which is also electricity conducting, cylindrical and arranged coaxially. The space between the outer sheath 4 and the core 6 is filled with a dielectric 8.

For the measurement of the viscosity of an epoxy resin or glycerol, the outer sheath 4 and core 6 are more particularly made from copper or steel lined with copper and the dielectric 8 is of Teflon.

Cable 2 has a small diameter, so as to be immersible in the medium to be checked. It has a diameter of $\leq 5$ mm and in particular 3.5 mm. This coaxial cable is a standard cable used in the ultra-high frequency range and one of its ends has a known connector 10 for fitting it in the ultra-high frequency measuring device, as shown in FIG. 5.

According to the invention, the end 12 of the core 6 of the cable 2, opposite to the connector 10, is bared over a length L, which can vary between 5 and 10 mm, as a function of the medium to be checked. In other words, the end 12 of the cable 2 has neither dielectric, nor outer sheath.

In the embodiment of FIG. 1, the bare end 12 of the sensor is rectilinear. This sensor, equipped with a single coaxial cable 2 operates in reflection. The measurement is a measurement of the reflected microwave power or the reflecting power:

$$R = \frac{\text{reflected power}}{\text{incident power}}$$

With a 7 mm long bare end and a microwave frequency of 4 GHz, we obtain $Pr = |0.15|^2 Po$ in glycerol with Pr being the reflected microwave power and Po the incident microwave power.

With the aid of a directional coupler 20 (FIG. 5), part of the microwave power reflected by the medium 22 is branched off to a microwave detection means 24, which supplies a voltage proportional to the reflected microwave power.

The structure according to FIG. 1 comes up against the following difficulty. If use is made of an ultra-high frequency source 26 (FIG. 5) operating at a fixed frequency Fo, e.g. a dielectric resonator oscillator, any frequency fluctuation leads to a fluctuation in the measured power due to parasitic reflections and interferences in the assembly.

In order to obviate this problem, it is merely necessary to use a frequency sweepable source and by forming the mean value of the detected power on the swept frequency range using a RC-type filter 28 (FIG. 5). The operation of the source 26 can be standardized by having a short-circuit in place of the sensor 2 and by regulating the level of the detected signal to a reference value with the aid of a regulatable attenuator 30 (FIG. 5).

The structure of FIG. 1 has the advantage of being usable in cases where the polymerization of the resin continues up to hardening, because the sensor can be recovered. In the case where the copper could interact with the material in which it is placed, the coaxial cable 2 can be given a silver or chromium plating in order to protect the copper.

As shown in FIG. 2, the sensor according to the invention can be constituted by two coaxial microwave cables 2a, 2b identical in all points to the coaxial cable 2 of FIG. 1 and equipped in each case with a connector respectively 10a and 10b. These cables are juxtaposed and welded by welds 14 distributed over the entire length so as to form an integral assembly. Said sensor operates in transmission, i.e. the incident microwave signal is carried by one of the two cables 2a or 2b and the microwave signal reflected by the viscous medium is received by the other cable 2b or 2a.

This transmission operation procedure makes it possible to use monochromatic microwave sources 26 (FIG. 5) without being impeded by the interferences occurring in reflection on the different microwave connections of the viscosity measuring device. However, the sensor of FIG. 2 has a larger volume than that of FIG. 1 and cannot be used with very viscous liquids because the latter cannot circulate in the space 15 separating the two sensitive ends 12a and 12b.

The sensor according to the invention can be produced in the manner shown in FIGS. 3 and 4. These structures are obtained by curving the bare, sensitive end 12c (FIG. 3) or 12d (FIG. 4) of a coaxial, microwave cable 2c or 2d, which is identical in all respects to that of FIG. 1, in order to form a magnetic loop, which can be square (FIG. 3) or circular (FIG. 4) and is closed. To this end, the end of the core 6c or 6d, respectively of the sensor 2c and 2d is welded to the conductive sheath 4c or 4d with the aid of a tin weld respectively 16c, 16d.

The surface of the loop is an adaptation element for the sensor in the same way as the length L of the bare ends 12 of the preceding structures. In particular, the dimension e of the square magnetic loop (FIG. 3) is between 2 and 5 mm.

Like the structure of FIG. 1, the structures of FIGS. 3 and 4 operate in reflection with the same constraints as those of FIG. 1, i.e. it is necessary to associate them with frequency sweepable source and to filter the detected signal in order to obtain the mean reflected power on the swept frequency interval or range. These structures have the advantage of a better sensitivity than that of FIG. 1 as a result of a better ultra-high frequency coupling between the sensor and the viscous medium.

With a magnetic loop having a surface of 28 mm$^2$ and a 4 GHz microwave frequency, $Pr = |0.28|^2 Po$ is obtained in glycerol with Pr and Po respectively representing the reflected and incident microwave power.

As stated hereinbefore, the aforementioned sensor forms part of a measuring device diagrammatically shown in FIG. 5 and essentially incorporating an ultra-high frequency or microwave source 26, checking elements such as an insulator 32 and an attenuator 30, a directional coupler or a circulator 20 in the case of reflection measurements and a detection means 24.

Microwave guides 34, 36, 38 and 40 ensure the microwave coupling respectively between the source and the attenuator, between the attenuator and the directional coupler, between the directional coupler and the connector 10 of the sensor and between the coupler and the detection means.

The specifications of each of these components will now be described.

1) Ultra-high frequency source 26:

Solid state sources, Gunn diodes or transistorized oscillators are very suitable for such measurements. They have the advantages of an ease of supply (10 or 15 v d.c.), a good stability (the power supplied remaining constant better than 1% under normal conditions of use) and a·long life.

These sources exist in two forms, namely dielectric resonator oscillators supplying power levels of a few dozen mW at a fixed frequency, chosen as required, and YIG-controlled oscillators (ultra-high frequency diode, which is well known to the Expert and which is made from yttrium garnet and iron) or varactors able to operate on varyingly wide frequency bands (several hundred MHz for varactor checking, several GHz for YIG checking). The control of said sources takes place by a voltage of 0 to 10 v using a function 50 l.f. generator.

In the present invention use is preferably made of a YIG-controlled oscillator, which makes it possible to choose an average operating frequency in a relatively wide band (e.g. 2 to 8, 8 to 12 or 12 to 18 GHz, and to have a frequency modulation on a 1 GHz band in order to obtain, in detection, a mean signal not affected by parasitic reflections. This modulation is produced by a voltage ramp of appropriate amplitude and a frequency which can vary from 10 Hz to 1 KHz. Moreover, this type of operation makes the measurement signal relatively insensitive to the fluctuations of the source (fluctuations of the supply voltages or modulation conditions).

2) The insulator 32 is an indispensable component, which is introduced into the source case indicated by the broken lines 33. It protects the source against reflections created in the complete ultra-high frequency circuit on e.g. dismantling the sensor. It makes it possible to have an operation of the source which is independent of what takes place in the remainder of·the circuit and particularly the reflection level at the end of the circuit. The reflection coefficient becomes equal to 1 on dismantling the sensor.

3) The function of the attenuator 30 is to modify the incident microwave power and consequently adapt the power to reference conditions fixed once and for all. It permits a standardization of the operating conditions of the circuit indispensable in industrial use. The reference level is regulated, as required, between 0 and 10 V with a stabilized current supply 41.

4) The directional coupler 30 separates the reflected wave from the incident wave and makes it possible to measure the reflected power. It can be replaced by a circulator in the case of a low reflected power. However, the separation of the two waves by a directional coupler is better than by a circulator, but the former only samples 10% of the reflected power (10 dB coupler), whereas the circulator transmits all of this to the detector 42.

5) The detector 42, which is of the Schottky diode or contact diode type, must be integrated in known manner into an assembly of a suitable type and must be protected against electromagnetic interference. The electric signal supplied by the detector 42 is supplied to an electronic circuit and is constituted by an amplifier 44 with a gain of approximately 100 and a RC-type low pass filter 28 with a time constant of approximately one second (large compared with the modulation frequency of the source).

At the outlet from said filter a continuous signal varying between 0 and 15 V is obtained and which is proportional to the mean power reflected in the frequency band used. This continuous signal can be used as such and can be supplied directly to a recorder or can be converted into a digital signal with the aid of an analog-digital converter 46 before being supplied to a microcomputer 48 for calculating the viscosity of the viscous medium.

As has already been stated, the measuring device and therefore the sensor can be calibrated as a function of the viscous medium to be checked and the constructional embodiment used for the sensor (FIGS. 1 to 4).

The inventors used as the test medium glycerol, because it has a relatively high viscosity at ambient temperature (close to 0.1 Pa·s, i.e. 1000 centipoises) and said viscosity is highly dependent on the temperature. Other tests were carried out on epoxy resins.

The operating conditions of the measuring device are that the average operating frequency of the ultra-high frequency device is chosen on the basis of a prior study making it possible to fix an optimum frequency between 2 and 18 GHz. For glycerol the frequency is between 2 and 4 GHz, whereas for epoxy resins it is around 9.5 GHz.

In addition, for glycerol, a mean frequency of 3.5 GHz is chosen. The microwave source 26 used is a YIG-controlled oscillator on a 2 to 8 GHz band. The control voltage is supplied by the function generator 50. It is a symmetrical sawtooth voltage varying between 1.2 and 3.7 V. The frequency of said modulation is 20 to 100 Hz. The measurement of the viscosity does not change if the modulation frequency varies. In the curves given hereinafter use is made of 20 and 50 Hz modulation frequencies.

The reference value of the measurement is e.g. defined by the signal obtained when the sensor is in place, but in air. This signal value is fixed at 10 V by means of the variable attenuator 30 placed in the circuit. It should be noted that for the reference value it is possible to use a short-circuit in place of the sensor, which makes it possible to check the reference during the measurement without having to clean the sensor.

FIG. 6 gives the variations of the viscosity $\eta$ in Pa·s of glycerol as a function of the voltage U (in volts) supplied at the output of the detection means 24 and which represents the power of the microwaves reflected by the medium.

Said same curve was obtained during several experiments by heating the glycerol in order to modify its viscosity. The measurement has a good reproducibility with all error sources coinciding (cleaning and putting back into place the sensor, fluctuations of the source, etc.). The fluctuation on a measurement remains below 20 mV for a signal of 1.80 mV. The accuracy on a viscosity measurement is then $25 \cdot 10^{-4}$ Pa·s (25 centipoises) between 500 and $1000 \cdot 10^{-4}$ Pa·s (i.e. between 500 and 1000 centipoises).

In the case of epoxy resins, the measurement frequency is 9.5 GHz. The variation of the signal is smaller than in the case of glycerol (300 mV for a 1000 centipoise variation), so that the accuracy is slightly less satisfactory and is approximately $50 \cdot 10^{-4}$ Pa·s (50 centipoises) for a viscosity varying from 500 to $1500 \cdot 10^{-4}$ Pa·s (500 to 1500 centipoises).

FIG. 7 gives the variations of the viscosity $\eta$ (in Pa·s) of a polymerizable epoxy resin as a function of the voltage U in volts supplied at the output of the detection means 24. The ordinate scale is 20 mV/cm, but the origins have been displaced in order that all the experimental points are on the same curve. This curve was obtained no matter what the measurement frequency used. This proves that the ratio of a variation of the microwave signal reflected by the viscous medium on the variation of its viscosity is independent of the frequency. This ratio represents the sensitivity of the measurement.

In this case said sensitivity is 6.8 mV/$10^{-1}$ Pa·s, as can be clearly gathered from FIG. 8, which gives the variations of the voltage U (in volts) supplied by the detection means 24 as a function of the microwave frequency F (in GHz) used for an epoxy resin with a viscosity of 0.1 Pa·s (3000 cps). The fluctuations on a microwave measurement are approximately 10 mV, so that it is possible to measure a viscosity to within approximately $13 \times 10^{-3}$ Pa·s (130 cps). This accuracy is of the same order of magnitude as that obtained with conventional rotary viscosimeters.

As stated hereinbefore, the relation linking the power Pr of the microwaves reflected on the sensor by the viscous medium with the dielectric properties of the medium is established by calibration. In the case of an epoxy resin, the power Pr is linked with the viscosity by a formula of the type:

$$Pr = k \log \cdot \eta + C,$$

in which C is a constant linked with the viscous medium and k a constant linked with the sensor.

The sensor according to the invention can operate in a viscosity range between $10^{-2}$ Pa·s (100 cps) and 10 Pa·s ($10^5$ cps.).

The range of use of the sensor according to the invention covers all polar liquid media and in particular dipolar polymers. The device according to the invention can in particular be used for checking the ageing of resins in impregnation tanks, checking the polymerization in thermal enclosures, checking the viscosity of adhesives, polymer-based paints, etc.

We claim:

1. Device for the continuous real time measurement of the viscosity of a polar viscous resin (22) said device comprising, in combination, a microwave source (26), a sensor having at least one semirigid, coaxial microwave cable (2, 2a, 2b, 2c, 2d) for immersion in the resin to be measured, and means (10, 10a, 10b) for connecting said sensor via a microwave guide to a microwave source, said cable having an outer sheath (4, 4c, 4d) and a core (6, 6c, 6d) which conduct electricity and which are arranged coaxially, the space defined between the sheath and the core being filled with a dielectric (8), said core having a bare end (12, 12a, 12b, 12c, 12d) for placement in contact with the viscous resin to be measured, said sensor producing in said medium incident microwaves of a given power and detecting the power of microwaves reflected by the resin, a detector (42) for transforming the power of the reflected microwaves into an electric signal which is a rising function of the viscosity, a first microwave guide (34, 36, 38) for coupling the microwave source to the sensor, and a second microwave guide (40) for coupling the detector to the sensor.

2. Device according to claim 1, wherein the sensor comprises a single coaxial cable (2, 2c, 2d).

3. Device according to claim 1, wherein the bare end (12c, 12d) of the sensor core is formed in a magnetic loop closed in short-circuit with the outer sheath (4c, 4d) of said sensor.

4. Device according to claim 1, wherein the core and outer sheath of the sensor are formed of copper, and the sensor dielectric is formed of polytetrafluoroethylene.

5. Device according to claim 1, wherein the coaxial cable has an external diameter below 5 mm.

6. Device according to claim 1, wherein the microwave source (26) is a YIG frequency controlled oscillator.

7. Device according to claim 1, further comprising a microwave insulator (32) connected between the microwave source (26) and the sensor.

8. Device according to claim 1, further comprising a microwave power attenuator (30) operationally connected between the microwave source and the sensor.

9. Device according to claim 1, further comprising a filter (28) for filtering the electric signal supplied by the detector (42).

10. Device according to claim 1, further comprising a directional coupler (20) between on the one hand the microwave souce (26) and the sensor and on the other hand the detector (42) and the sensor, when said sensor comprises a single coaxial cable (2, 2c, 2d).

11. Device according to claim 1, wherein the microwave source is frequency modulated on a 1 GHz frequency band around the operating frequency.

12. Device according to claim 1, characterized in that the detector for transforming the power of the reflected microwaves into an electrical signal is a diode selected from the group consisting of contact diodes and Schottky barrier diodes.

13. Device according to claim 4, and further comprising a silver plating over the copper.

14. Device according to claim 4, and further comprising a chromium plating over the copper.

* * * * *